(12) United States Patent
Hoerstrup et al.

(10) Patent No.: US 11,285,244 B2
(45) Date of Patent: Mar. 29, 2022

(54) ALIGNED POROUS FIBRILLAR SCAFFOLD FOR TISSUE ENGINEERING AND SURGICAL APPLICATION

(71) Applicants: ETH ZÜRICH, Zürich (CH); UNIVERSITÄT ZÜRICH, Zürich (CH)

(72) Inventors: Simon Philipp Hoerstrup, Zürich (CH); Seyedvahid Hosseini, Watt (CH); Viola Vogel, Baden (CH)

(73) Assignees: ETH ZÜRICH, Zürich (CH); UNIVERSITÄT ZÜRICH, Zürich (CH)

( * ) Notice: Subject to any disclaimer, the term of this patent is extended or adjusted under 35 U.S.C. 154(b) by 100 days.

(21) Appl. No.: 16/347,200

(22) PCT Filed: Oct. 27, 2017

(86) PCT No.: PCT/EP2017/077700
§ 371 (c)(1),
(2) Date: May 3, 2019

(87) PCT Pub. No.: WO2018/083047
PCT Pub. Date: May 11, 2018

(65) Prior Publication Data
US 2020/0054793 A1      Feb. 20, 2020

(30) Foreign Application Priority Data
Nov. 3, 2016  (EP) ..................................... 16197169

(51) Int. Cl.
*A61L 27/56*    (2006.01)
*A61L 27/18*    (2006.01)
*A61L 27/34*    (2006.01)

(52) U.S. Cl.
CPC ............... *A61L 27/56* (2013.01); *A61L 27/18* (2013.01); *A61L 27/34* (2013.01);
(Continued)

(58) Field of Classification Search
CPC ........... A61L 27/56; A61L 27/18; A61L 27/34
(Continued)

(56) References Cited

U.S. PATENT DOCUMENTS

| 10,588,997 | B2 * | 3/2020 | Pokorski ............... A61L 15/425 |
| 2015/0265746 | A1 * | 9/2015 | Martin .................... A61L 31/06 |
| | | | 424/1.65 |

(Continued)

FOREIGN PATENT DOCUMENTS

| JP | 2001-527101 | 12/2001 |
| JP | 2002-539854 | 11/2002 |

(Continued)

OTHER PUBLICATIONS

Bo Wang et al, "The effect of poly (L-lactic acid) nanofiber orientation on osteogenic responses of human osteoblast-like MG63 cells", Journal of the Mechanical Behavior of Biomedical Materials Jan. 21, 2011 (Jan. 21, 2011), vol. 4, No. 4, p. 600-609 (Abstract only).

(Continued)

*Primary Examiner* — Suzette J Gherbi
(74) *Attorney, Agent, or Firm* — JMB Davis Ben-David (57) ABSTRACT

The invention relates to a method for preparing a polymer scaffold that comprises the steps of providing a piece of a fabric of filaments of a first biodegradable or biocompatible polymer, applying a coating of a second polymer to said arrangement of filaments, and stretching the piece along its axis of longitudinal extension, thereby obtaining an aligned microfibrillar scaffold. The invention further relates to a method for providing an artificial tissue, and to a microfi- (Continued)

brillar scaffold of aligned filaments obtained by the method of the invention.

20 Claims, 8 Drawing Sheets

(52) U.S. Cl.
 CPC ....... *A61L 2420/02* (2013.01); *A61L 2430/10* (2013.01); *A61L 2430/20* (2013.01); *A61L 2430/30* (2013.01); *A61L 2430/32* (2013.01)

(58) Field of Classification Search
 USPC ........................................... 623/23.71–23.76
 See application file for complete search history.

(56) References Cited

U.S. PATENT DOCUMENTS

| | | | | |
|---|---|---|---|---|
| 2017/0056544 | A1* | 3/2017 | Pokorski | A61L 15/44 |
| 2018/0320290 | A1* | 11/2018 | Masuda | D01F 8/00 |
| 2019/0038796 | A1* | 2/2019 | Pokorski | A61L 27/34 |
| 2019/0175781 | A1* | 6/2019 | Pokorski | A61L 15/44 |
| 2020/0179096 | A1* | 6/2020 | Allen | D01D 5/0084 |
| 2020/0390933 | A1* | 12/2020 | Williams | B29C 48/05 |
| 2020/0390944 | A1* | 12/2020 | Williams | D01D 5/08 |

FOREIGN PATENT DOCUMENTS

| | | |
|---|---|---|
| JP | 2009-524507 | 7/2009 |
| WO | 9932536 | 7/1999 |
| WO | 0056376 | 9/2000 |
| WO | 2007090102 | 8/2007 |

OTHER PUBLICATIONS

Zhang Shen et al, "[Improved mechanical strength and cell occlusivity of electrospun L-polylactic acid aligned nanofibrous membranes by post heat treatment].", Medline Oct. 2011 (Oct. 2011), Database accession No. NLM22097262 Retrieved from the Internet: URL:US National Library of Medicine (NLM), Bethesda, MD, US.

Mol A et al, "Fibrin as a cell carrier in cardiovascular tissue engineering applications", Biomaterials Jun. 1, 2005 (Jun. 1, 2005), vol. 26, No. 16, p. 3113-3121.

* cited by examiner

ALIGNED POROUS FIBRILLAR SCAFFOLD FOR TISSUE ENGINEERING AND SURGICAL APPLICATION

CROSS-REFERENCE TO RELATED APPLICATIONS

This is the U.S. National Stage of International Patent Application No. PCT/EP2017/077700 filed on Oct. 27, 2017, which was published in English under PCT Article 21(2), and which in turn claims the benefit of European Patent Application No. 16197169.2 filed on Nov. 3, 2016.

The present invention relates to a method for making a biodegradable or biocompatible polymer scaffold for attachment of eukaryotic cells in the generation of artificial tissue or surgical implantation of polymeric scaffold for proper tissue healing. The invention further relates to the scaffold generated by the method of the invention, and the artificial tissue derived thereof.

DESCRIPTION

Tissues and cells in vivo are mostly organized in a preferred orientation, which forms in development and morphogenesis. For engineered tissues, where the aim is to replicate tissue function in in vitro conditions, achieving specific cellular organization can influence the future functionality of the engineered tissue. Some examples include parallel alignment of muscle fibers, collagen fibers in tendon and helical alignment of vascular smooth muscle cells. For example, accumulative micro contractions of organized muscle fibers enable achieving strong contractions, and in load bearing tissues such as tendons and heart valves, parallel alignment of collagen fibers as part of the extracellular matrix (ECM) significantly improves the toughness of the tissue. Moreover, in soft tissues such as spinal cord, aligned organization of axons is needed to transfer stimuli in the correct direction similar to the native organization to improve the repair of neural cord injuries.

Tissue engineering and surgical reconstruction application making use of three dimensional (3D) cellular growth require proper scaffolds to assure in vivo functionally. Early induction of in-vitro cellular alignment is important, as cells can hardly remodel mature matrix after ECM deposition and maturation of collagen fibrils.

Different methods are currently used to induce cell alignment. A first approach is based on confining cells on an engineered surface or material having a micro-nanotopography as contact guidance. A second approach is based on application of mechanical forces generated either by the contractile activity of the cells or by an external strain, thus inducing alignment. External mechanical forces such as stretching stress, which can be applied to a surface, e.g. an elastomeric sheet with seeded cell or flow shear stress (friction) over cells in endothelial cell culture can also induce alignment. These methods, however, are restricted to two-dimensional organization, in which few cell layers grow on top of each other. 3D cell alignment in hydrogel systems is limited to a few cell layers due to the lack of nutrition perfusion within the hydrogels.

Commercially available unwoven felt-like polyglycolic acid (PGA) scaffold (Biofelt®) has been made by melt spinning of PGA fibers and further carding and needle-punch processing. This process is performed using industrial machinery; therefore the prepared scaffold is available in different shapes, sizes and can be made from different bioresorbable polymers. This solvent-less process is less risky than solvent casting procedures like as electrospinning but less practiced to develop scaffolding materials because of the processing difficulties. Importantly and in contrast to electrospun scaffolds, it results in high porosity of around 90% and has successfully demonstrated the ability to rapidly grow cells and form 3D tissue structures. In situ tendon regeneration as well as homeostatic cardiac and abdominal wall surgeries were reported using PGA meshes as scaffolding material. However, such melt-spun scaffolds have never been used to prepare 3D aligned tissues mainly due to scaffold integrity problems. Fiber alignment techniques used for electrospinning will result in fiber integrity loss of melt-spun scaffolds having microfibers (diameter~15 µm).

Based on the above-mentioned state of the art, the objective of the present invention is to provide means and methods to provide methods and materials useful for 3D cell culture and subsequent generation of artificial tissue. This objective is attained by the claims of the present specification.

Terms and Definitions

The term biodegradable polymer or a bioresorbable polymer in the context of the present specification relates to a polymer that will be degraded actively (by enzymatic hydrolysis) or passively (by chemical hydrolysis) in the human body, or under conditions of cell culture, within a time frame ranging from days to years. A biodegradable polymer is characterized by two qualities: the polymer is slowly lysed to its constituent monomer parts, or derivatives thereof, under physiological conditions within a biological meaningful time frame, and the products of this degradation are not toxic, at least at the concentrations occurring under conditions of lysis, to the organism in which they are contained. The time required for degradation or resorption depends on the nature of the polymer, the site of implantation and the dimensions and porosity of the polymer. Typical biodegradable or bioresorbable polymers are PLA, PGA, PGLA or polybutyric acid.

The term biocompatible polymer in the context of the present specification relates to a polymer that is tolerated within a human body, without necessarily being lysed. Non-degradable scaffolds can be used for example in reconstructive/cosmetic surgery and as a guidance of neurons in spinal cord repair surgery. Neurons cannot produce protective tissue and therefore need to be protected by in situ supports. In neurosurgery, neural growth is supported by providing an aligned scaffold as well and at the same time support the mechanical integrity by a non-degradable scaffold.

The terms polyglycolide and PGA in the context of the present specification relate to the polymer poly[oxy(1-oxo-1,2-ethanediyl)] (CAS No. 26009-09-0), described by a general formula particularly the polymer of the above formula wherein n is between 900 and 1200, or wherein the mean molecular mass of the polymer is approx. 60.000 g/mol.

The terms poly(lactic acid), polylactic acid and PLA in the context of the present specification relate to the polyester of lactic acid (CAS No 26100-51-6), described by the general formula particularly the polymer of the above formula wherein n is between 700 and 1000, or wherein the mean molecular mass of the polymer is approx. 60.000 g/mol.

The terms poly-3-hydroxybutyrate or P3HB in the context of the present specification relate to the polyester of 3-hydroxybutyric acid, which is a strong thermoplastic polyester that, despite its biosynthetic route, has a relatively simple structure. Particular preparations of P3HB useful herein are characterized by a mean molecular mass of 400.000-600.000 g/mol.

The terms poly-4-hydroxybutyrate or P4HB in the context of the present specification relate to the polyester of 4-hydroxybutyric acid, which is a strong thermoplastic polyester that, despite its biosynthetic route, has a relatively simple structure. Particular preparations of P4HB useful herein are characterized by a mean molecular mass of 400.000-600.000 g/mol.

The term glass transition temperature or Tg in the context of the present specification relates to the range of temperatures over which the glass transition, a reversible transition in amorphous materials from a hard and relatively brittle "glassy" state into a molten or rubber-like state occurs as the temperature is increased. The Tg values given herein relate to values determined by the differential scanning calorimetry methods, unless stated otherwise. For the measurement protocoll, see ISO 11357-2; Plastics—Differential scanning calorimetry (DSC)—Part 2: Determination of glass transition temperature (1999).

The term index of alignment in the context of the present specification relates to the percentage of fibers counted by microscopy that have angles ±20 degree to the axis of stretching, in relation to total fiber count.

The term porosity of a porous material as used herein relates to the standard parameter known in material science, which is calculated as 1 (or 100%) minus the ratio of bulk (b) to material (or scaffold, sc) sample density: $\Phi = 1 - \rho_b/\rho_{sc}$.

DESCRIPTION OF THE INVENTION

The invention relates to a process of making a scaffold of highly aligned microfibres that is characterized by a porosity sufficient to allow the growth of mammalian cells. Typical values of porosity are in the range exceeding 75%, 80%, 85% or even around 90%.

According to a first aspect, the invention relates to a method for preparing a polymer scaffold, comprising the steps of
   a. providing a piece of a fabric of filaments of a first polymer, wherein said first polymer is biodegradable or biocompatible, and wherein said piece is characterized by an axis of longitudinal extension;
   b. applying a coating of a second polymer to said arrangement of filaments, wherein said second polymer is characterized by a glass transition temperature that is lower than the melting point of said first polymer; and subsequently
   c. stretching said piece along its axis of longitudinal extension, thereby aligning said filaments,
      whereby an aligned microfibrillar scaffold is obtained.

In certain embodiments, the piece of a fabric of filaments of a first polymer is a non-woven fabric mesh. In certain embodiments, piece of a fabric of filaments of a first polymer is a felt-like textile.

It is possible to employ woven fabrics as textile also, as long as the knitting or weaving technique allows textile to be stretched in one axis. Displacement of fibers to find a new orientation in the woven textile is important to achieve the desired fiber alignment. Therefore not all knitting techniques are suitable for application of this invention, but the skilled person will be able to select textiles that are amenable to the process of the present invention by the guidance offered herein.

In certain embodiments, the piece of fabric is stretched along its axis of longitudinal extension in step c to more than 175%, i.e. a 10 cm long piece would be stretched to 17.5 cm or longer. In certain embodiments, the piece of fabric is stretched to between 175% and 250% or even to 300%. In certain embodiments, the piece of fabric is stretched to approx. 200%.

The degree of stretching sufficient to attain the required alignment in the filaments varies significantly. It depends on the nature of the first polymer fibre, its processing and degree of entanglement. Degrees of stretching effective in attaining the alignment leading to the advantages of the present invention have varied from 110% to 1000% stretch in various materials.

In certain embodiments, the stretching process can be quantified by applying a measure of alignment prior to and after stretching in step c. Thereby, the piece of fabric going into the process is characterized by a first index of alignment $i_{A1}$ of the filaments, and the aligned microfibrillar scaffold is characterized by a second index of alignment $i_{A2}$ after stretching in step c.

The ratio $i_{A2}/i_{A1}$ of the second index of alignment to the first index of alignment is a measure of the degree to which the fabric has been stretched. In certain embodiments, this ratio is greater than 2, particularly 2.5 and more particularly greater than 3.

In certain embodiments, the alignment index as defined above is 20-25% for random scaffold, 55-60% for a sample stretched to 150% of its pre-stretch length (1.5×), and 75-80% for a sample stretched to 200% of its pre-stretch length (2.0×).

Scaffolds obtained by simple microfiber stretching combine a high porosity with pores sufficiently large to allow cell invasion, which offers an advantage over nanofibers. Alignment of microfibers, however, will result in their disintegration. Application of the second polymer prevents this destruction of the fibre meshwork, which allows to combine a high porosity of microfibres and their alignment in materials that are amenable to cell migration and culture. In certain embodiments, the first and second polymer are each characterized by a glass transition temperature Tg and a melting temperature Tm, and step c. is performed at a temperature that is higher than the Tg of both the first and second polymer, and lower than the Tm of both the first and second polymer. In other words, in order to effect the alignment, the polymers must both have been heated beyond their glass transition point in order to be sufficiently plastic, but must not have melted.

In certain embodiments, the first polymer may not have a defined Tm. The skilled person understands that the main point of the process temperature is to conduct the process at a temperature below the melting point of the scaffold matrix, but above the glass transition point of both polymers.

In certain embodiments, step c. is performed at a temperature between 50° C. and 150° C., particularly between 60° C. to 80° C. These temperatures work particularly well for PGA (and/or poly-L-lactic acid (PLLA) and PLGA) based scaffolds.

In certain embodiments, the scaffold is cooled down after step c. prior to releasing the applied tension.

In certain embodiments, the second polymer is a biodegradable and/or a biocompatible polymer.

In certain embodiments, the amount of the second polymer applied to the filaments ranges from 10% to 40% (mass %; m/m) in relation to the mass of the filaments of the first polymer. For example, 10 g of a fabric comprised of PGA filaments will have a mass of between 13 g after being coated with polyhydroxybutyrate, amounting to the application of 30% of second polymer.

In one particular embodiment, an amount of 10% to 40% of second polymer is applied by deep coating of the first polymer scaffold in a solution of 2% (w/v) polyhydroxybutyrate in THF.

In certain embodiments, the first polymer is selected from the group comprising a polyester, a polyurethane and a polyaniline. In certain embodiments, the first polymer is selected from the group comprising polyglycolide (PGA), poly(lactic acid) (PLA), polylacticglycolic acid (PLGA), poly(trimethylene carbonate) (PTMC), and a copolymer comprising glycolic acid or lactic acid monomers.

Polyaniline is a conductive polymer (PANI) used in biosensor technology. It is not biodegradable but biocompatible. PANI is contemplated here as a suitable material for building permanent scaffolds for use in addressing spinal cord injury, particularly for its utility in guiding the neural growth or applying stimulation to severed nerves.

In certain embodiments, the first polymer is selected from the group comprising a polyethylene glycol (PEG); a polyethylene terephthalate (PET); poly(2-methoxyethyl acrylate) (PMEA); poly(2-methacryloyloxyethyl phosphorylcholine) (PMPC); poly(tetrahydrofurfuryl acrylate) PTHFA); and polystyrene (PST).

The second polymer serves to coat the first polymer's filament and keeps them aligned after the stretching force is released. The second polymer is different from the first polymer. It is applied by dip coating in solution; it is evident that the solvent or polymer itself must not dissolve the first polymer. The second polymer can be selected from the list given for the first polymer, with the proviso that the second polymer must dissolve in a solvent that does not entirely dissolve the first polymer under the conditions applied.

In certain embodiments, a solvent is used that can dissolve both polymers, but at least the first one is dissolved only very slowly under the condition in which the second polymer is applied.

For example, a polymer solution of the second polymer can be obtained by overnight dissolution, which is then applied on the first polymer by flash dipping in solution, after which the scaffold is put in a vacuum to dry. The first polymer, which will be high molecular weight, is not dissolved to the point of disintegrating the structure, and the coating of second polymer remains on the first one and forms in the fibers interjunction.

In certain embodiments, the second polymer is a polyhydroxybutyrate, particularly P4HB and P3HB. As one non-limiting example, P4HB can be dissolved in THF (Tetrahydrofuran) to coat fibres of PGA, PLA, PLLA, and PLGA.

Further advantageous combinations of first polymer, second polymer and solvent are given, by way of non-limiting examples, in the Table 1:

| $1^{st}$ Polymer | $2^{nd}$ Polymer | Solvent for $2^{nd}$ polymer |
| --- | --- | --- |
| PGA | PLA | THF |
| PGA | PLGA | THF, Dioxane |
| PGA | PTMC | THF, Chloroform |
| PGA | P4HB | THF, Acetone |
| PGA | P3HB | THF, Acetone |
| PLA | PGA | THF, Dioxane |
| PLA | PLGA | THF, Dioxane |
| PLA | PTMC | THF, Chloroform |
| PLA | P4HB | THF, Acetone |
| PLA | P3HB | THF, Acetone |
| PTMC | PLA | THF |
| PTMC | PLGA | THF, Dioxane |
| PTMC | PGA | THF, Dioxane |
| PTMC | P4HB | THF, Acetone |
| PTMC | P3HB | THF, Acetone |
| P4HB | PLA | THF, Dioxane |
| P4HB | PLGA | THF, Dioxane |
| P4HB | PGA | THF, Dioxane |
| P4HB | PTMC | THF, Chloroform |
| P4HB | P3HB | THF, Acetone |
| P4HB | PEG | THF, Acetone |
| P3HB | PLA | THF |
| P3HB | PLGA | THF, Dioxane |
| P3HB | PGA | THF, Dioxane |
| P3HB | P4HB | THF, Acetone |

In certain embodiments, the filaments are characterized by a diameter of between 100 nm and 250 µm, particularly between 1 µm and 50 µm, more particularly between 10 µm and 20 µm.

In certain embodiments, the piece of fabric provided in step a. is characterized by a scaffold specific density of 5 to 15% in relation to the bulk density of the first polymer. In certain embodiments, the piece of fabric obtained in step c. is characterized by a scaffold specific density of 10% to 20% in relation to the bulk density of the first polymer. In certain embodiments, the piece of fabric obtained in step c. is characterized by a scaffold specific density, measured in relation to the bulk density of the first polymer, being 1.5 to 3 times, particularly approx. 2 times, greater than the scaffold specific density of the piece of fabric provided in step a.

The porosity of the material can be calculated from scaffold density and bulk density values employing the formula $\Phi = 1 - \rho_b/\rho_{o\chi}$.
wherein is $\rho_b$ the density of the bulk material, and $\rho_{o\chi}$ is the density of the porous scaffold.

Another aspect of the invention relates to an ex-vivo method for providing an artificial tissue, comprising the steps of a. providing an aligned microfibrillar scaffold according to the method laid out above as the first aspect of the invention, in any of its embodiments; and b. suspending the aligned microfibrillar scaffold in a cell culture medium comprising mammalian cells.

In certain embodiments, the mammalian cells are selected from fibroblasts, myoblasts and neurons. In certain embodiments, the cell culture medium compromises all nutrients and growth factor for cell growth and differentiation at 37 degree centigrade and the cells were kept in culture up to 20 days.

Yet another aspect relates to an aligned microfibrillar scaffold of filaments of a first biodegradable or biocompatible polymer coated with a second biodegradable or biocompatible polymer, characterized in that
  a. the porosity of said scaffold is greater or equal (≥) 80%, particularly ≥85%, more particularly ≥90%.
  b. the alignment index is greater 50%, particularly ≥75%, more particularly ≥85%, and/or
  c. the diameter of said filaments ranges from 100 nm to 250 µm, particularly from 5 µm to 50 µm, more particularly from 10 µm to 20 µm.

Particular applications, such as scaffolds applied for bone regeneration, may be characterized by lower porosity values, such as for example 50%.

In certain embodiments, the fibres or filaments constituting the scaffold are characterized by a diameter ranging from 5 µm to 50 µm, inclusive.

The parameter of fiber or filament diameter is important with regard to create pores that are accessible for cell infiltration. For example, with fiber in nanometer range, aligned scaffolds can be created even with 90% porosity. The problem of such nanometre high porosity scaffolds, however, is that they are characterized by a high number of pores that are too small for cells to infiltrate. Micrometer range microfiber random scaffolds with good pore sizes for cell infiltration are known in the art, however these fibres lack the necessary alignment.

Therefore accessibility of pores in highly porous scaffolds should be assessed separately. Other examples of non-fibrous scaffold, such as foams and hydrogels, both usually have more than 95% porosity but their pores are not sufficiently accessible for cell infiltration. Therefore, these scaffolds need to be made in situ in the presence of cells.

In certain embodiments of this aspect of the invention, the first polymer is selected from the group comprising a polyester, a polyurethane and a polyaniline.

In certain embodiments, the first polymer is selected from a first group comprising the biodegradable polymers, particularly the group comprising polyglycolide, poly(lactic acid), PLGA, poly(trimethylene carbonate), poly(4-hydroxybutyrate), poly(3-hydroxybutyrate), poly(glycolide-co-caprolactone), poly(glycolide-co-trimethylene carbonate), or a copolymer comprising glycolic acid or lactic acid monomers.

In many applications, this first polymer, if selected to be biodegradable, will be combined with a second (coating) polymer that is also biodegradable in order to render the entire scaffold biodegradable.

In certain embodiments of this aspect of the invention, the first polymer is selected from a second group comprising non-biodegradable, but biocompatible polymers, particularly polymers selected from the group consisting of polyaniline, polyethylene glycol (PEG); polyethylene terephthalate; poly(2-methoxyethyl acrylate); poly(2-methacryloyloxyethyl phosphorylcholine); poly(tetrahydrofurfuryl acrylate); polystyrene, or a copolymer of two or three different polymers comprised in this second group, particularly a copolymer of PEG with any of the other second group non-biodegradable polymers.

In certain embodiments of this aspect of the invention, the second polymer is a polyhdydroxybutyrate, particularly selected from P4HB and P3HB.

In certain embodiments of this aspect of the invention, the scaffold is characterized by a scaffold specific density of 10 to 20% in relation to the bulk density of the first polymer.

To conclude, the inventors herein report a novel approach to induce fiber alignment in microfibrillar polymeric scaffolds while maintaining scaffold porosity and fiber integration. Such polymeric scaffolds are frequently used for tissue engineering and surgical applications and provide a suitable platform for 3D cell and tissue culture. The simple approach presented herein provides a universal method for fiber alignment in fibrillar scaffolds. The cell studies provided in the examples illustrate the suitability of the method of the invention for growing millimeter scale 3D aligned tissue constructs, allowing for cell and matrix alignment along the scaffold fiber direction. The method of the invention is suitable for application in many areas of tissue engineering and reconstructive surgeries where true 3D induction of cell alignment within a scaffold is required, including heart and skeletal muscle, tendon, nerves, and vascular tissue repair and engineering.

The scaffold provided by the methods disclosed herein can either be used for making an artificial tissue in-vitro, or can be used directly as surgical patch to encourage directed tissue healing and repair. Scaffolds provided for the second aspect (as patches) can be applied without prior incubation in cell culture.

Another aspect of the invention relates to the surgical application or in vivo application of the scaffold disclosed herein, either by direct implantation of the scaffold without cells or ECM directly into the body, which is expected to guide new tissue generation and thereby improve the healing process.

Wherever alternatives for single separable features such as, for example, an first polymer or second polymer, porosity or cell type are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

BRIEF DESCRIPTION OF THE FIGURES

FIG. 1 shows the production of aligned PGA scaffolds and fibre alignment analysis. (a) Illustration of the process of inducing alignment in random PGA meshwork by heating up the scaffold above Tg and below Tm, followed by application of unidirectional strain by using a stretching device (b). Width and length of rectangle shaped random PGA scaffold changed upon applying different stretches (50% and 100%). (c) Alignment analysis of differently stretched PGA scaffolds. (d) False colour fluorescence images and (e) electron microscopy micrographs of corresponding scaffolds visualizing highly aligned PGA scaffold upon 100% stretch with P4HB interconnections. Double head arrows show the direction of applied strain and small arrows show P4HB coating interconnecting PGA fibers. Scale bars (a) 5 mm, (d) 200 µm (e) 50 µm.

FIG. 4 shows fibronectin matrix assembled by rabbit tendon fibroblasts and its alignment quantification after three weeks of culture on random and aligned PGA scaffolds. Maximum Z projection intensity of multi-plane confocal images of fibronectin matrix assembly on (a, b, c) aligned and (d, e, f) random PGA scaffolds (gray) visualized by incorporation of labeled fibronectin (green) in the culture medium during 3 weeks of culturing, showing fibronectin deposition between and around the PGA fibres (g) Quantification of alignment of fibrillar fibronectin bundles along the scaffold's fibre direction show higher level of anisotropy within aligned PGA scaffolds. (h, k) Cross-sectional view of cultured scaffolds are showing the fibronectin matrix formation take place across the scaffold independent to scaffold type and preferentially higher fibronectin deposited in the sides confronted to the flow (white arrows).

EXAMPLES

The inventors report herein a simple method to induce microfiber alignment on a centimeter scale using commercially available biodegradable/resorbable polymers, particularly PGA. As an exemplary embodiment, the inventors used an unwoven PGA mesh. The method of the invention can basically be applied to any other microfibrillar scaffold.

Firstly, PGA fibres were coated with Poly4-hydroxybutyrate (P4HB), then heated above the glass transition temperature (Tg) of both polymers and aligned by applying unidirectional strain to the PGA-P4HB meshwork. As a result of the applied strain, the PGA fibers uncoiled and individual fibres aligned parallel to the strain axis. Such aligned PGA microfibers meshwork was used as a scaffold to guide cellular organization and initiate cell alignment into its porous structure. The results presented herein demonstrate that such a porous and aligned scaffold offers 3D cellular infiltration and is able to efficiently align cells by contact guidance, while preserving the 3D organization. Moreover, using a perfusion device and efficient cell seeding due to the suitable scaffold porosity, enabled the inventors to obtain aligned 3D microtissues. This approach is not limited to the presented example and applicable to other fibrillar scaffolds that are in use for tissue engineering, reconstructive surgery and basic cell studies.

Figure 1:
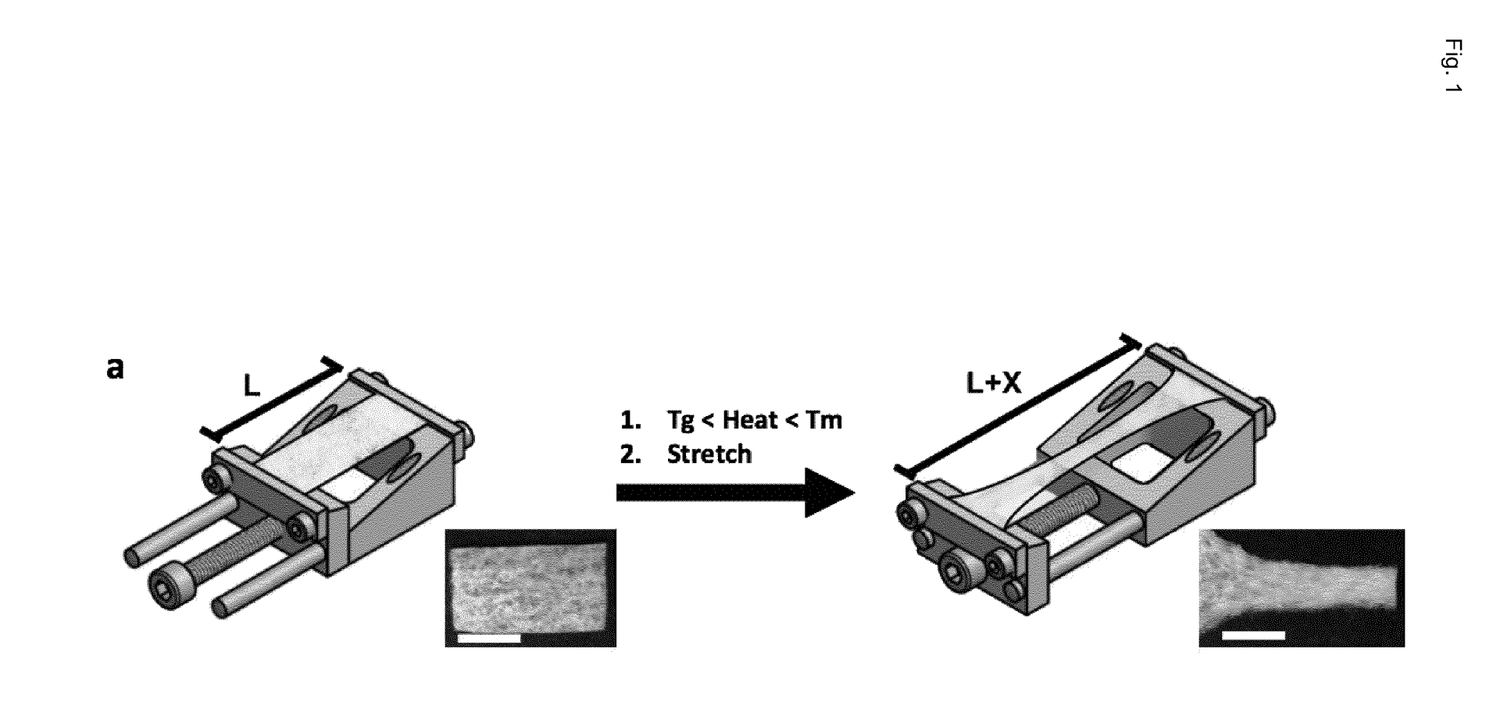

Example 1: Stretching of P4HB Coated PGA Scaffold Above Tg Uncoils the Meshwork and Induces Fibre Alignment PGA has a transition temperature ($T_g$) of 35-45° C. and a melting point ($T_m$) of 220-230° C., while the $T_g$ and $T_m$ of Poly4-hydroxybutyrate (P4HB) vary from 5-15° C. and 168-182° C., respectively. The PGA scaffold is coated with P4HB by immersing it in P4HB solution (1.75% in tetrahydrofuran (THF), followed by overnight drying at ambient temperature. Addition of P4HB extends the degradation time of the PGA fibres, acting as a protecting layer on the scaffold when used for tissue engineering applications and at the same time improves scaffold integrity by bridging crossed fibres. Heating the scaffold up to 80° C., over the $T_g$ of both polymers, led to softening of the scaffold fibres and the P4HB, thus allowing application of unidirectional strain without inducing fibre breakage and damaging the scaffold. Successive reduction of the temperature below the $T_g$ of PGA to e.g. room temperature resulted in solidifying and setting the fibre meshwork in a new arrangement, with the P4HB component still interconnecting the fibres and preserving the scaffold integrity (FIG. 1a). On macro-scale, unidirectional strain resulted in deformation of the rectangular shape of the polymer meshwork by decreasing its width and increasing its length. In contrast to plastic films, the change in shape of the PGA meshwork was almost that observed for elastic films and showed distribution of width decrease over the entire length of the stretched scaffold, rather than being accumulated in a small part in the middle (FIG. 1a). This behaviour makes this processing approach suitable for obtaining an aligned scaffold from larger area of initially randomly oriented scaffold (FIG. 1). Macroscopic measurement showed width reduction of maximum 53% and 73% associated to 50% and 100% length increase with stretching, respectively (FIG. 1b). Scaffold thickness increased from 858±55 µm for unstrained condition to 1170±172 µm and 1036±191 µm for 50% and 100% stretched PGA conditions, respectively. In order to quantify fibre alignment, we analysed 3D fluorescence confocal images. For 100% stretched samples, 53% of fibres aligned (±10 degrees) to the axis strain, while 50%) stretch resulted in 34% of fibre aligned. Non-stretched PGA meshwork had only 14% fibres aligned to the axis strain (FIGS. 1c and d). Electron microscopy micrographs also confirmed PGA fibre alignment, and the existence of P4HB interconnections to the PGA fibres after applying stretch (FIG. 1e, white arrows).

Figure 2:
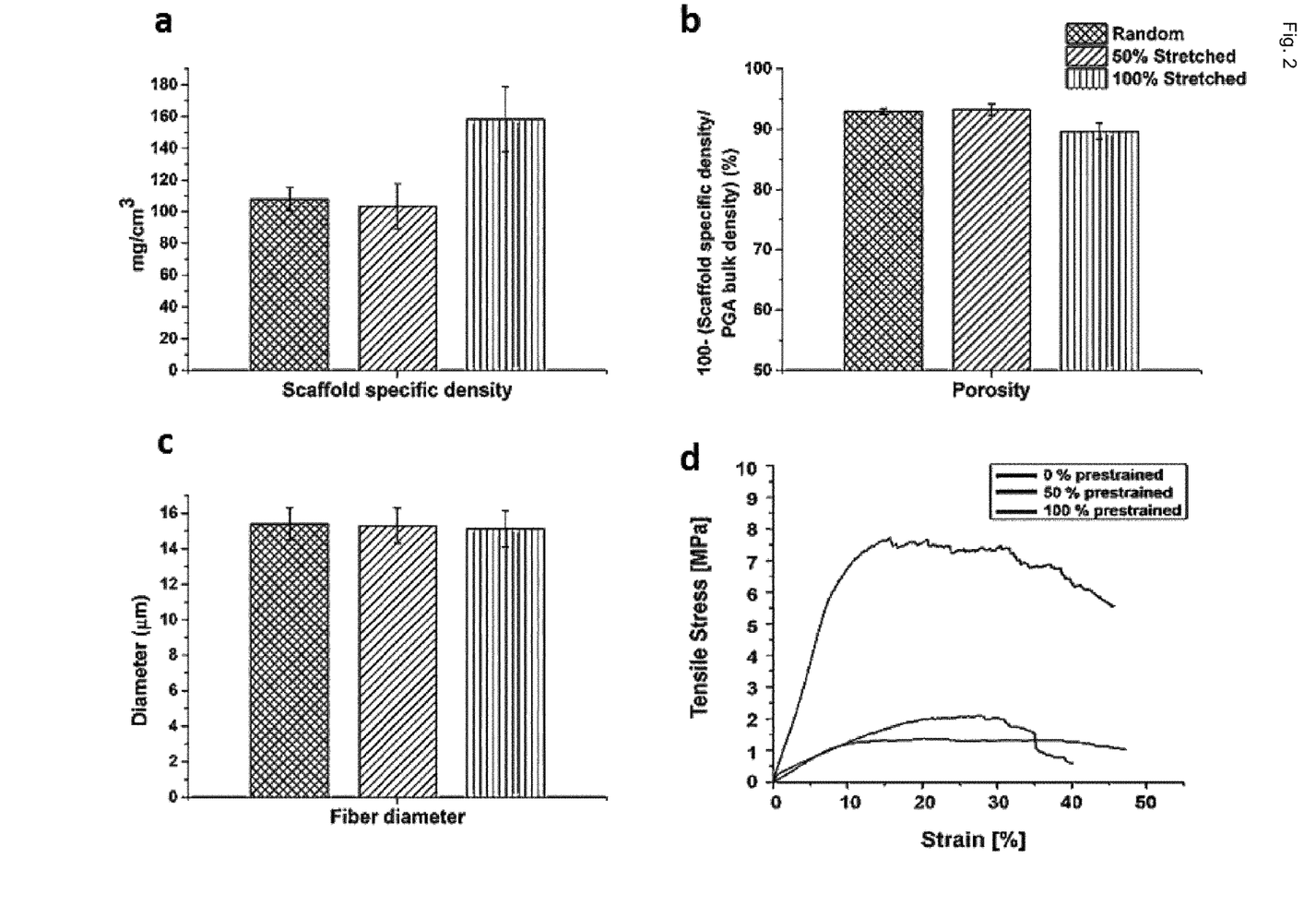
FIG. 2 shows changes in the physical properties of stretched and aligned PGA scaffolds. (a) Specific density [$mg/cm^3$] significantly increased after 100% stretching of a PGA scaffold. (b) Scaffolds porosity (reversely proportional to specific density) of a PGA scaffold. (c) Fibre diameter was not affected by external strain in processing of the random PGA scaffold. (d) Strain-stress curve for differently stretched PGA scaffolds, showing strong increase in the slope of the curve (Young's modulus) for 100% stretched PGA scaffold.

Scaffold density measurements showed no significant change in specific density for unstrained (105±6.9 mg/cm3) and 50% stretched (102±18.3 mg/cm$^3$) scaffolds, while significant increase was observed for 100% stretched (157.4±28.2 mg/cm$^3$) scaffolds (FIG. 2a), which is still far lower than density of bulk PGA polymer (1530 mg/cm$^3$). Porosity measurement for the scaffolds was performed, assuming as if the same volume of scaffold was filled with bulk PGA. Calculation of scaffold porosity showed 92.9±0.5%, 93.2±0.9% and 89.6. 8±1.3% porosity for 0, 50 and 100% stretched scaffolds, respectively (FIG. 2b), which signifies around 90% porosity of the scaffolds and a reverse trend as for the specific density measurements. Fiber diameter analysis did not show any significant changes in the fiber diameter for the differently stretched PGA scaffolds, meaning that the applied strain to the scaffolds did not affect the individual fibers directly in the process (FIG. 2c). Finally, the mechanical properties of the differently aligned fibrillar PGA scaffolds were measured and compared to the original PGA scaffold (FIG. 2d). Slight increase in young's modulus for 50% stretched scaffold (12.9 MPa) compared to the original scaffold (11.3 MPa) was observed, while stretching the PGA meshwork 100% increased the Young's modulus to 96.3 MPa. Strain at break for the random original PGA scaffold was around 40%, suggesting that heating the scaffold above the $T_g$ is a crucial point in order to stretch this type of scaffolds up to 100%.

The role of the second polymer, particularly P4HB, in the integrity of the first polymer (particularly: PGA) fibers is important particularly if the scaffold planned to be directly seeded with cell suspension or implanted to the body for further cell infiltration. Electron microscopy images (FIG.

1c, small arrows) show the inter-fiber areas filled with P4HB polymer. These polymeric bridges maintain the fiber network connections during stretching and behave like as elastic glue, stabilizing the meshwork. After the stretching process, these interconnections highly deformed under the strain, but still maintained the connection (FIG. 1 d, e). The deformability sourced from the $T_g$ of P4HB, which is slightly below room temperature, together with the annealing process at 80° C. helped in the deformation and shaping of this polymer. Stretching the PGA scaffold without the coating layers or dissolving the coating after stretching process showed scaffold integrity, which indicates the important role of secondary polymer coating.

Figure 3:
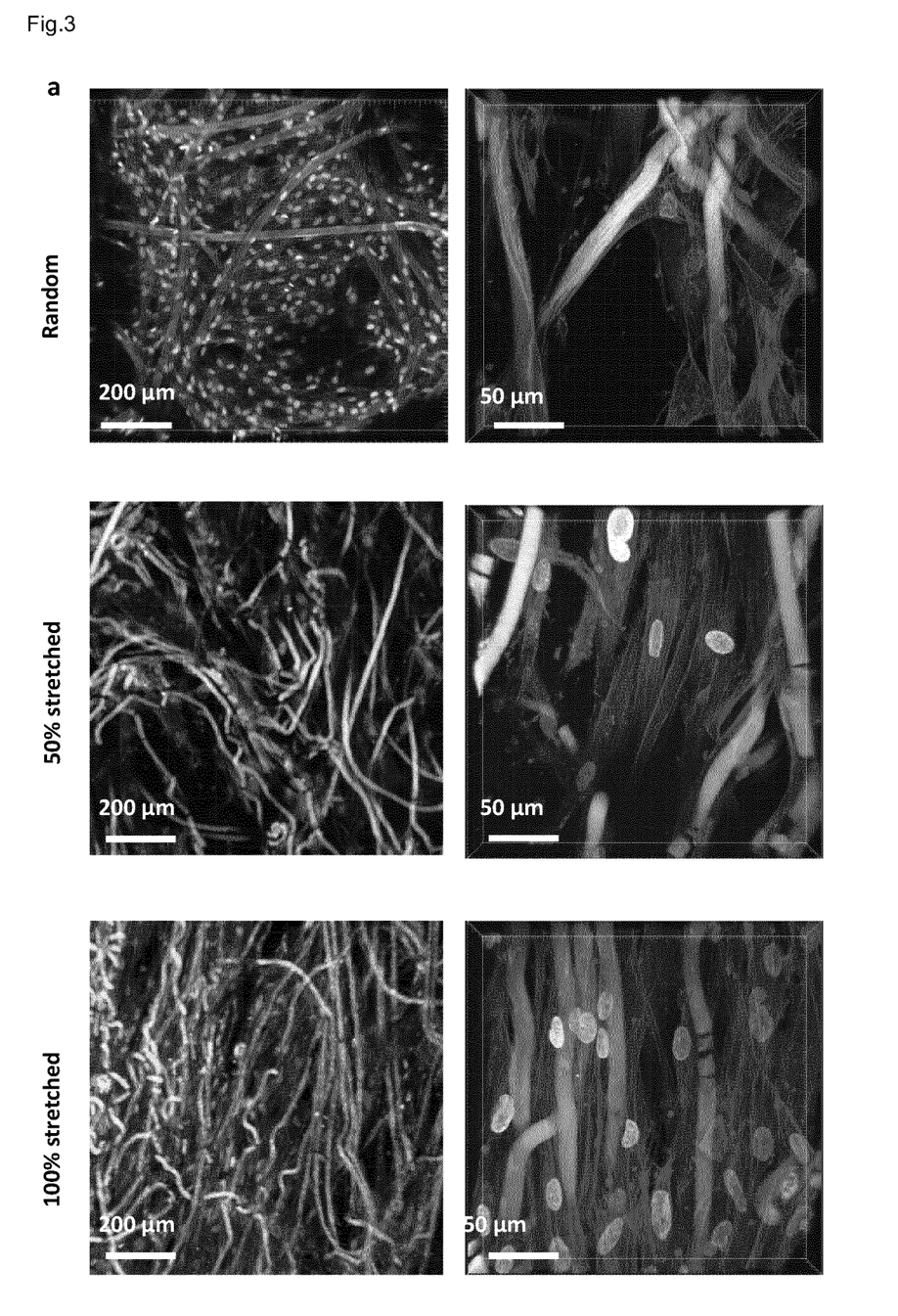
FIG. 3 shows cell nuclei and F-actin alignment analysis after 1 week of culturing of ovine vascular fibroblasts on differently stretched PGA scaffolds. (a) Maximum Z projection intensity of multi-plane confocal images of vascular fibroblasts stained for F-actin (violet) and nuclei (blue) seeded on differently stretched PGA scaffolds are showing cells growing between and over the fibrillar scaffolds and are quantified as noted according to their respective actin fibre alignment, indicating the alignment induction by aligned fibrillar scaffolds, percentage of aligned actin fibres and cell nuclei within ±10 degree of strain axis, indicating improved F-actin and cell nuclei alignment in stretched samples compared to randomly oriented PGA scaffolds. Scale bars: 200 µm (a, left) and 50 µm (a, right).

Example 2: Cells Embedded in 3D Aligned, Porous PGA Scaffolds, were Guided and Aligned to the Direction of the PGA Fibers To ensure that cells can grow and receive enough nutrients from the medium when seeded into the scaffolds, the inventors employed a simple circular shaker to perfuse the tissue during the cell culture period. Such bioreactor enabled us to grow cells in rather thick tissue sheets up to 1 mm thickness. Initially, ovine vascular fibroblasts were cultured in the device using PGA-P4HB scaffold in a period of one week. Afterwards, actin fibers and nuclei alignment were analyzed (FIGS. 3a and b). The analysis showed that majority of actin stress fibers aligned in the 100% stretched PGA scaffolds (FIG. 3b). From the counted aligned actin fibers, 51.1±5.7% were aligned with ±10 degree to the stretching axis of the PGA fibers in the 100% stretched scaffolds, 37.6±6.5% for the 50% stretched scaffolds, and 6.9%±4.7 for the randomly oriented PGA scaffolds (FIG. 3b, c). In addition, cell nuclei alignment analysis showed 52.6±10.2%, 36.9±13.6% and 14.4±3.7%) of aligned cell nuclei with ±10 degree to stretching axis of the PGA fibers, for the 100%, 50% and nonstretched PGA scaffolds, respectively (FIG. 3d), supporting the results obtained in the actin fiber alignment analysis.

Three Dimensional Depositions of Fibronectin Matrix Across the Scaffold

Figure 4:
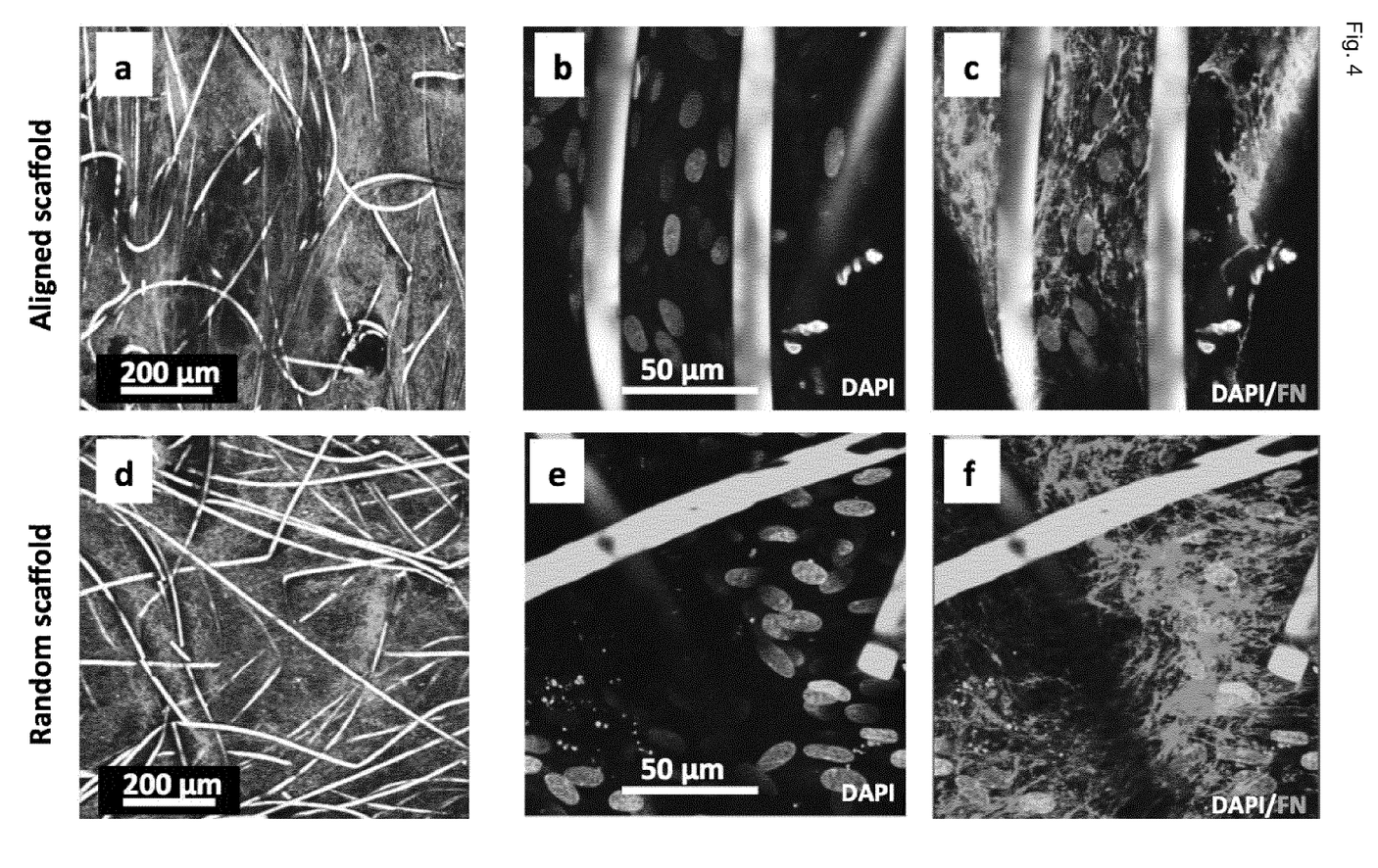

Although most of the studies on alignment report cell nuclei or actin alignment for short time period (hours-few days), the inventors evaluated not only cell nuclei and actin fiber alignment after a week, but also fibronectin fibrillar bundle alignment as a major ECM component, after three weeks. To do this, AlexaFluor0488 labelled fibronectin was added to the culture medium of rabbit tendon fibroblasts over a period of three weeks. During the culturing time, the labeled fibronectin perfused and co-assembled into ECM, thus allowing visualization of the fibronectin fibrillar network across the scaffold and was used to analyze the orientation angle of fibronectin fibrils (FIG. 4). Quantification of fibrillar fibronectin bundle alignment was done in 100% stretched samples (designated "aligned scaffold" in FIG. 4) and random PGA scaffold. To do this, high-resolution images first were analysed for contained objects ("thresholded"), then angle of major axis of threshold objects were defined as the orientation angle of bundles. Assembled fibronectin matrix on aligned PGA scaffold showed higher alignment when compared to random PGA scaffold (FIG. 4a-g). Slight preferential alignment in random PGA scaffold, however, is visible, which might result from parallel flow direction to the axis of alignment and/or tissue contraction. Cross sectional images (FIG. 4 e, f), were used to show how the fibronectin deposited across the scaffold, presenting the three dimensionality of the constructs and suitability of the pore size of the scaffolds for efficient cell seeding and infiltration. Although fibronectin was deposited across the scaffold, the deposition was pronounced in the sides, which confronted the flow (arrows in images h, k), indicating enhanced perfusion at the front side. Assessment of three weeks old ECM could be important as the ECM is stabilized at this age and previously has been shown that such tissue is suitable for harvesting and implanting into animals. Also, decellularization and further implantation of ECM scaffolds is another option that recently gained attention and revealed promising results in animal and human clinical studies. Usually decellularization of engineered tissue can be done after 4 to 8 weeks of in vitro culture which is considered suitable window for harvesting high quality ECM for further processing. A short-term 2D recellularization of decellularized ECM also showed that cells are able to align along deposited fibronectin fibers and follow the fiber directionality. Taking this into account, analysis of three weeks old fibronectin matrix performed here, could forecast the final cellular alignment outcomes, which will be one point of interest for future clinical applications. Furthermore, maintaining alignment after three weeks could be a forecasting index in which the in vivo implantation of such a scaffold possibly has sufficient time to guide new tissue formation.

Decellularized Aligned ECM Guides Further Cell Alignment, an Application for "Off-the-Shelf" Decellularized Engineered Tissues Decellularized tissue-engineered matrices from PGA or other polymeric scaffolds may be of use in vascular and heart valve tissue engineering, particularly as readily available "off"-the-shelf alternatives to xeno- and homografts in emergency conditions and developing countries. In this context, the inventors investigated if aligned ECM after the decellularization process is able to induce cell alignment. To do this, nano-patterned ridges on polydimethylsiloxane (PDMS) surfaces were replicated from silicon-SU8 mold. The mold was produced by conventional photolithographic approach and generously provided by Dr. Aldo Ferrari. PDMS surfaces had grooves with depth of 350 nm, width of 500 nm and ridge width of 500 nm. Nano-patterned PDMS surfaces were coated with Fibronectin (50 µg/ml), then human foreskin fibroblasts (HFFs) were seeded onto the coated surfaces. After cell adhesion, AlexaFlour® 488 labelled fibronectin was added to the cell culture medium (5 µg/ml) and cells were allowed to assemble the extracellular matrix for 3 days. After 3 days, the surfaces were decellularized using 0.5% Triton X100 in pH 8.5 for 15 minutes, thus obtaining decellularized ECM matrices. Afterwards, the acellular ECM scaffolds were reseeded with HFFs and incubated for 24 h. Here, 2D surfaces instead of 3D constructs were used in order to ease the imaging, de- and recellularization processes. Incorporating AlexaFlour® 488 labelled fibronectin (by adding the labeled fibronectin in the medium) offered easy visualization of how the fibronectin fibrillar bundles aligned along the groove's direction compared to flat surface. Reseeding of fibroblasts on fibronectin ECM after the decellularization process revealed that the newly seeded cells are capable to align along the direction of the assembled matrix, demonstrating that the old ECM is capable of initiating cell alignment (actin alignment) and serve as a topographical guidance. This finding supports the application of pre-aligned decellularized matrix as an alternative matrix for off-the-shelf applications, in which further recellularization and cell alignment could be triggered by pre-aligned decellularized matrix.

Comparative Example 3

A PLGA polymer solution having a final polymer concentration of 6 wt % was prepared by dissolving PLGA in a mixture of chloroform and ethanol (75:25 w/w). The polymer was dissolved overnight at room temperature and solutions were stirred for 30 minutes before use in order to obtain homogeneity.

For the production of electrospun scaffolds, an in-house assembled electrospinning device was used, consisting of a spinning head with a blunt end made of stainless steel tube (1 mm inner diameter and 0.3 mm wall thickness, Angst & Pfister AG, Zürich Switzerland), a DC high voltage supply (Glassman High Voltage Inc., High Bridge, N.J., USA), hollow cylindrical rotating aluminum mandrel as a collector and a syringe pump (AL1000 Aladdin, World Precision Instruments, Inc., Germany). The polymer solution was loaded into a 5 mL syringe (B. Braun Melsungen AG, Germany) and pumped into the spinning head with 0.7 mL/h flow rate. A voltage of 11 kV was applied and the distance between the spinning head and the collector was fixed to 15 cm. The produced scaffolds were collected on an aluminum foil and dried under vacuum overnight at room temperature. Then the fabric were collected from AL foils and installed on manual stretcher device. Afterwards the fabric was heated up to 60 degree Celsius and stretched 2× (200%). In this comparative example the second polymer was not applied. Upon stretching the fiber coils were opened up and aligned with alignment index of 80%. However, upon release of tension on the fabric, the fiber integrity and alignment was lost due to absence of secondary polymer. The fiber diameter was determined to range from 1-2 μm. This comparative example illustrates that the invention can be applied on other type of random fabric produced by other techniques like as electrospinning and the importance of application of second polymer coating to preserve the integrity of fabrics.

Material and Methods:

Scaffold Preparation

A commercially available nonwoven PGA scaffold (thickness 1.0 mm; specific gravity 70 mg/cm$^3$; Biofelt, Bereldange Luxembourg) was coated with 1.75% poly-4-hydroxybutyrate (P4HB; MW: 100000; TEPHA Inc., Lexington Mass. USA) in tetrahydrofuran (Sigma-Aldrich, St Louis Mo. USA). P4HB was added to increase the meshwork integrity and slowdown the degradation rate of PGA. To prepare the aligned PGA scaffold, piece of PGA scaffold was mounted on the stretching device and heated in oven at 80° C. for 2 minutes. After removing the specimens from the oven, they were stretched manually and as fast as possible either to 1.5× or 2× from their original length. Afterwards, scaffolds were cooled down to room temperature and used for future analysis and cell culture studies.

Alignment Analysis of PGA Meshwork

To visualize the PGA fibers, the autofluorescence properties of PGA fibers upon excitation at 405 nm or 488 nm were imaged with laser scanning confocal microscopy (Olympus, FV1000, Japan). After obtaining images of PGA scaffolds, the fiber orientation was determined using ImageJ software. Briefly, the fiber angle was calculated in every scanned plane via the particle analyzer option in ImageJ, in ten degree increments (0 to 90 degrees) and the number of fibers for each increment was counted and presented as an average percentage (%) from the total number of fibers.

Scaffolds Specific Density and Porosity Analysis

The specific density of the PGA scaffolds was determined gravimetrically, namely the weight of the scaffold was divided with the total volume of the scaffold. The length and width of the scaffolds were measured by ruler, while their thickness was measured from their cross section using bright field microscopic images. Results are presented in mg/cm$^3$. Moreover, the scaffold porosity was calculating by dividing the scaffold specific density to bulk density of PGA (1530 mg/cm$^3$) and presented as percentage.

Mechanical Analysis

The mechanical properties of the differently stretched PGA scaffolds were obtained from stress/strain curves measured using a uniaxial load test machine (Instron tensile tester, High Wycombe, Buck, UK: model 5864) equipped with a 100 N load cell. Samples with rectangular shape and a testing region of 10×2 mm$^2$ and thickness range of 800-1200 μm were used. Elongation rate of 20 mm/min was applied until failure. The Young's modulus [MPa] and strain at break [%] were determined for every condition (n=3).

PGA Scaffold Installation in Mini-Bioreactor

To effectively allow cell growth in the 3D environment of the PGA scaffold, we developed a simple pulsatile flow minibioreactor. Our previous study has shown that this bioreactor improved ECM deposition on engineered PGA scaffolds when compared to static conditions (citation). Briefly, the PGA scaffold was fixed on the peripheral wall of a petri dish (5 cm diameter), using a UV optical glue (Norland optical adhesive, NJ, USA). The scaffold was moving forward and backward by each pulse of the orbital shaker. After attaching the scaffold, a mixture of 10% hydrogen peroxide in 70% ethanol and UV light were used for 1 hour to sterilize the setup. The whole setup were washed at least 3 times with sterile PBS and let to dry out, followed by overnight incubation in culture medium consisting of DMEM-Glutamax (Invitrogen, USA) supplemented with 10% fetal bovine serum (FBS, Invitrogen, USA), 1% Penicillin/Streptomycin (P/S, Invitrogen, USA) and 50 μg/ml L-ascorbic acid (Sigma, USA) before cell seeding.

Cell Seeding and Conditioning of PGA Scaffold

Human venous myofibroblasts were harvested from the vena saphena magna and expanded as model for vascular engineering and for cell alignment analysis. In addition, rabbit tenocytes from the Achilles tendon, isolated and cultured as previously described (Evrova et al., Macromolecular Bioscience 2016, 19, 1048), were used as a model to reconstruct engineered tendons. Cell seeding was done using fibrin gel as a carrier, as previously described (Mo et al., Biomaterials 2005, 26, 3113). Briefly cells were defrosted, expanded and trypsinized as for standard cell culture protocols. Afterwards, cells were resuspended in a sterile bovine thrombin (Sigma, USA) solution in PBS (10 IU thrombin/ml). Fibrinogen solution was prepared by dissolving 14 mg of lyophilized bovine fibrinogen powder (Sigma, USA), equal to 10 mg/ml active fibrinogen into culture medium and the solution was filter sterilized using 0.21 μm sterile filter. Subsequently, the cells in the thrombin solution were added to the sterile bovine fibrinogen solution in equal volume. After brief mixing, the fibrin solution containing the cells was pipetted onto the PGA scaffold. The coagulation time of the fibrin gel was determined to vary from 20 to 40 s. Therefore, constructs were allowed to polymerize for 15 min at 37° C. and 10% CO$_2$ before culture medium was added. All the constructs were cultured under static conditions for the first 24 hours and afterwards perfusion was started, using orbital shaker (VWR, USA) and a mini bioreactor platform. The rotation radius of the shaker was 19 mm and rotation speed of 1 Hz (60 rpm) was applied to all the samples during the study. Culture medium was exchanged every 3 days by replacing half of the medium and adjusting the evaporated medium by sterile deionized water. Incubation was done at 37° C. and 10% CO$_2$ for optimized DMEM buffering during the study.

Imaging of Cells and Extracellular Matrix on PGA Scaffolds

After the specific culturing period, the samples were immunostained for actin, and nuclei. For immunostaining, samples were washed with PBS and then fixed in 4% Paraformaldehyde in PBS for 30 min. Non-specific adsorption of antibody was prevented by adding albumin (BSA, 2% w/v, 30 min). Actin cytoskeleton was stained using Alexaflour® 488 conjugated phalloidin (Invitrogen, USA). Cell nuclei were stained with DAPI (2 µg/ml, 10 min). Samples were finally washed 3 times with PBS and imaged.

Cell Nuclei, F-Actin and Fibronectin Alignment Analysis

Cell nuclei alignment was analyzed using confocal images and particle analyzer option in ImageJ. As the autofluorescence of the PGA fibers interferes when using the 405 nm laser, nuclei were segmented by circularity, size and furthermore manually checked in all samples. After defining the orientation angle of the nuclei, nuclei with ±10 degree to the axis of stretch of the fibers, i.e. preferred fiber direction were counted and presented as aligned cell nuclei.

Similar approach was used to analyze the alignment of actin cytoskeleton and fibrillar network of fibronectin bundles, using high-resolution confocal images. First the images were thresholded to define actin fiber or fibronectin bundle perimeter. Then ImageJ particle analyzer was employed to define long axis of each particle and its orientation angle. These angles were defined as orientation angle of actin fiber and fibronectin bundles. The orientation angle of actin or fibronectin was then categorized in 5 degree bins to obtain the histograms for angles between 0 and 180 degree. Actin fibers with ±10 degree to the stretch axis of PGA fibers were assumed as aligned actin fibers.

Statistics

Data were compared using one way ANOVA with post hoc Bonferoni test (PASW statistics 18 software). Error bars represent standard deviation. p values ≤0.05 were considered to be statistically significant.

The invention claimed is:

1. A method for preparing a polymer scaffold, comprising the steps of
   a. providing a piece of a fabric, of filaments of a first polymer, wherein said first polymer is biodegradable or biocompatible, and wherein said piece is characterized by an axis of longitudinal extension;
   b. applying a coating of a second polymer to said arrangement of filaments in a coating step, wherein said second polymer is characterized by a glass transition temperature being lower than the melting point of said first polymer;
   c. stretching said piece along its axis of longitudinal extension,
thereby obtaining an aligned microfibrillar scaffold, wherein the first and second polymer are each characterized by a glass transition temperature Tg and a melting temperature Tm, and step c. is performed at a temperature that is
   higher than the Tg of both the first and second polymer, and
   lower than the Tm of both the first and second polymer.

2. The method according to claim 1, wherein in step c, said piece of fabric is stretched along its axis of longitudinal extension by more than 175%.

3. The method according to claim 1, wherein
   prior to stretching in step c, said piece of fabric is characterized by a first index of alignment $i_{A1}$ of said filaments, and wherein
   after stretching in step c, said aligned microfibrillar scaffold is characterized by a second index of alignment $i_{A2}$, and wherein
   the ratio $i_{A2}/i_{A1}$ of said second index of alignment to said first index of alignment is equal or greater than (≥) 2.

4. The method according to claim 3, wherein
   the value of $i_{A1}$ is ≤30%, and/or
   the value of $i_{A2}$ is ≥70%, and/or
   the value of the ratio $i_{A2}/i_{A1}$ is ≥2,3.

5. The method according to claim 1, wherein step c. is performed at a temperature between 50° C. and 150° C.

6. The method according to claim 1, wherein
   a. said second polymer is a biodegradable and/or a biocompatible polymer, and/or
   b. the amount of said second polymer applied to said filaments ranges from 10% to 40 mass % in relation to the mass of said filaments of said first polymer.

7. The method according to claim 1, wherein
   a. the first polymer is selected from the group comprising a polyester, a polyurethane and a polyaniline, and/or
   b. the second polymer is selected from a first group or a second group, but is different from the first polymer;
      the first group comprising polyglycolide, poly(lactic acid), PLGA, poly(trimethylene carbonate), polyhydroxybutyrate, poly(4-hydroxybutyrate), poly(3-hydroxybutyrate), poly(glycolide-co-caprolactone), poly(glycolide-co-trimethylene carbonate), or a copolymer comprising glycolic acid or lactic acid monomers, or from
      the second group comprising a polyethylene glycol (PEG) or a PEG copolymer; a polyaniline; a polyethylene terephthalate; poly(2-methoxyethyl acrylate); poly(2-methacryloyloxyethyl phosphorylcholine); poly(tetrahydrofurfuryl acrylate); polystyrene, or a copolymer comprising or essentially consisting of two or three polymer species comprised in the second group.

8. The method according to claim 7, wherein the second polymer is selected from
   a. the first group mentioned in claim 7 a if the first polymer is selected from the first group mentioned in claim 7 a, or
   b. the second group mentioned in claim 7 a if the first polymer is selected from the second group mentioned in claim 7 a.

9. The method according to claim 1, wherein in the coating step, said second polymer is applied as dissolved in a solvent to said filaments of the first polymer, and the first polymer and the second polymer are selected from one line of the following Table,

| $1^{st}$ Polymer | $2^{nd}$ Polymer | Solvent for $2^{nd}$ polymer |
| --- | --- | --- |
| PGA | PLA | THF |
| PGA | PLGA | THF, Dioxane |
| PGA | PTMC | THF, Chloroform |
| PGA | P4HB | THF, Acetone |
| PGA | P3HB | THF, Acetone |
| PLA | PGA | THF, Dioxane |
| PLA | PLGA | THF, Dioxane |
| PLA | PTMC | THF, Chloroform |
| PLA | P4HB | THF, Acetone |
| PLA | P3HB | THF, Acetone |
| PTMC | PLA | THF |
| PTMC | PLGA | THF, Dioxane |
| PTMC | PGA | THF, Dioxane |
| PTMC | P4HB | THF, Acetone |
| PTMC | P3HB | THF, Acetone |
| P4HB | PLA | THF, Dioxane |

-continued

| 1st Polymer | 2nd Polymer | Solvent for 2nd polymer |
|---|---|---|
| P4HB | PLGA | THF, Dioxane |
| P4HB | PGA | THF, Dioxane |
| P4HB | PTMC | THF, Chloroform |
| P4HB | P3HB | THF, Acetone |
| P4HB | PEG | THF, Acetone |
| P3HB | PLA | THF |
| P3HB | PLGA | THF, Dioxane |
| P3HB | PGA | THF, Dioxane |
| P3HB | P4HB | THF, Acetone | and optionally, the solvent is selected from the same line of said Table.

10. The method according to claim 1, wherein said filaments are characterized by a diameter of between 100 nm and 250 µm.

11. The method of claim 1, wherein
a. the piece of fabric provided in step a. of claim 1 is characterized by a scaffold specific density of 5% to 15% in relation to the bulk density of the first polymer; and/or
b. the piece of fabric obtained in step c. of claim 1 is characterized by a scaffold specific density of 10% to 20% in relation to the bulk density of the first polymer; and/or
c. the piece of fabric obtained in step c. of claim 1 is characterized by a scaffold specific density, measured in relation to the bulk density of the first polymer, being ≤30% greater than the scaffold specific density of the piece of fabric provided in step a of claim 1.

12. An ex-vivo method for providing an artificial tissue, comprising the steps of
a. providing an aligned microfibrillar scaffold according to the method of claim 1;
b. suspending said aligned microfibrillar scaffold in a cell culture medium comprising mammalian cells.

13. A microfibrillar scaffold of aligned filaments of a first biodegradable or biocompatible polymer coated with a second biodegradable or biocompatible polymer, characterized in that
a. the porosity of said scaffold is greater or equal (≥) 80%,
b. the alignment index is higher than (≥) 50%, and/or
c. the diameter of said filaments ranges from 100 nm to 250 µm.

14. The microfibrillar scaffold according to claim 13, wherein
a. the first polymer is selected from
a first group comprising polyglycolide, poly(lactic acid), PLGA, poly(trimethylene carbonate), poly(4-hydroxybutyrate), poly(3-hydroxybutyrate), poly(glycolide-co-caprolactone), poly(glycolide-co-trimethylene carbonate), or a copolymer comprising glycolic acid or lactic acid monomers, or from
a second group comprising a polyethylene glycol (PEG) or a PEG copolymer; a polyaniline; a polyethylene terephthalate; poly(2-methoxyethyl acrylate); poly(2-methacryloyloxyethyl phosphorylcholine); poly(tetrahydrofurfuryl acrylate); polystyrene, or a copolymer comprising or essentially consisting of two or three polymer species comprised in the second group,
and/or
b. the second polymer is selected from the first group or the second group given in the preceding paragraph, but is different from the first polymer.

15. The microfibrillar scaffold according to claim 13, wherein the scaffold is characterized by a scaffold specific density of 10 to 40% in relation to the bulk density of the first polymer.

16. The method according to claim 1, wherein in step c, said piece of fabric is stretched along its axis of longitudinal extension by between 175% and 300%.

17. The method according to claim 3, wherein
the value of $i_{A1}$ is ≤25%, and/or
the value of $i_{A2}$ is ≥75% and/or
the value of the ratio $i_{A2}/i_{A1}$ is ≥3.

18. The method according to claim 1, wherein
a. the first polymer is selected from
a first group comprising polyglycolide, poly(lactic acid), PLGA, poly(trimethylene carbonate), polyhydroxybutyrate, poly(4-hydroxybutyrate), poly(3-hydroxybutyrate), poly(glycolide-co-caprolactone), poly(glycolide-co-trimethylene carbonate), or a copolymer comprising glycolic acid or lactic acid monomers, or from
a second group comprising a polyethylene glycol (PEG) or a PEG copolymer; a polyaniline; a polyethylene terephthalate; poly(2-methoxyethyl acrylate); poly(2-methacryloyloxyethyl phosphorylcholine); poly(tetrahydrofurfuryl acrylate); polystyrene, or a copolymer comprising or essentially consisting of two or three polymer species comprised in the second group,
and / or
b. the second polymer is a poly-hydroxybutyrate.

19. The method according to claim 1, wherein said filaments are characterized by a diameter of between 1 µm and 50 µm.

20. The method of claim 1, wherein
a. the piece of fabric provided in step a. of claim 1 is characterized by a scaffold specific density of 5% to 15% in relation to the bulk density of the first polymer; and/or
b. the piece of fabric obtained in step c. of claim 1 is characterized by a scaffold specific density of 10% to 20% in relation to the bulk density of the first polymer; and/or
c. the piece of fabric obtained in step c. of claim 1 is characterized by a scaffold specific density, measured in relation to the bulk density of the first polymer being ≥50% greater than the scaffold specific density of the piece of fabric provided in step a of claim 1.

* * * * *